(12) United States Patent
Salvi et al.

(10) Patent No.: US 7,431,703 B2
(45) Date of Patent: Oct. 7, 2008

(54) APPARATUS AND METHOD FOR MEASURING AND MONITORING RANGE OF MOTION OF THE LUMBAR SPINE

(76) Inventors: Frank J. Salvi, 4363 Damascus Trail, Cottage Grove, WI (US) 53527; John G. Webster, 1710 Hoyt St., Madison, WI (US) 53726; Gabriel J. Donatell, 2206 Kendall Ave., Apartment B, Madison, WI (US) 53726; David W. Meister, 137 Running Farm La., #102, Stanford, CA (US) 94305; Jeremy R. O'Brien, 711 N. 16th St., #201, Milwaukee, WI (US) 53233; John S. Thurlow, 905 S. Claremont 3F, Chicago, IL (US) 60612

( * ) Notice: Subject to any disclaimer, the term of this patent is extended or adjusted under 35 U.S.C. 154(b) by 0 days.

(21) Appl. No.: 10/799,334

(22) Filed: Mar. 12, 2004

(65) Prior Publication Data
US 2005/0203443 A1 Sep. 15, 2005

Related U.S. Application Data

(60) Provisional application No. 60/455,249, filed on Mar. 15, 2003.

(51) Int. Cl.
*A61B 5/117* (2006.01)
*A61B 5/103* (2006.01)

(52) U.S. Cl. .................................................. 600/594

(58) Field of Classification Search .................. 600/546, 600/587, 594, 595
See application file for complete search history.

(56) References Cited

U.S. PATENT DOCUMENTS

| | | | | |
|---|---|---|---|---|
| 4,730,625 A | * | 3/1988 | Fraser et al. ................. | 600/594 |
| 5,012,819 A | * | 5/1991 | Marras et al. ................ | 600/594 |
| 5,143,088 A | * | 9/1992 | Marras et al. ................ | 600/594 |
| 5,146,929 A | * | 9/1992 | Sawhill ....................... | 600/594 |
| 5,337,758 A | * | 8/1994 | Moore et al. ................. | 600/594 |
| 5,398,697 A | * | 3/1995 | Spielman ..................... | 600/594 |
| 5,400,800 A | * | 3/1995 | Jain et al. ..................... | 600/595 |
| 5,772,610 A | * | 6/1998 | McGorry et al. ............. | 600/594 |
| 5,826,578 A | * | 10/1998 | Curchod ....................... | 600/595 |
| 5,989,201 A | * | 11/1999 | Brunner ....................... | 600/595 |
| 6,554,781 B1 | * | 4/2003 | Carter et al. ................. | 600/594 |

* cited by examiner

*Primary Examiner*—Max Hindenburg
*Assistant Examiner*—Brian Szmal
(74) *Attorney, Agent, or Firm*—Joseph W. Byrne

(57) ABSTRACT

An apparatus and method for detecting, monitoring, measuring and recording the motion of a patient's spine is disclosed. The apparatus includes a vertical member attached to a belt that fits around the patient's waist. A first sensor for detecting and monitoring flexion and extension of the patient's spine in the midsagittal plane is mounted to the lower end of the vertical member. A second sensor for detecting and monitoring lateral bending and movement of the patient's spine in the frontal plane is mounted to the upper end of the vertical member.

11 Claims, 3 Drawing Sheets

APPARATUS AND METHOD FOR MEASURING AND MONITORING RANGE OF MOTION OF THE LUMBAR SPINE

This application claims the benefit of U.S. Provisional Application No. 60/455,249, filed Mar. 15, 2003.

FIELD OF THE INVENTION

The present invention relates generally to an apparatus and method for monitoring patient movement and range of motion. More specifically, it relates to an apparatus and method for detecting, monitoring, measuring, and recording the motion of a patient's spine in a plurality of directions or planes.

BACKGROUND OF THE INVENTION

Patients suffering from low back pain are typically placed on an exercise regime by their physician or by a physical therapist assigned to work with the patient. The exercise regime is designed to strengthen the patient's back muscles, to improve the patient's overall range of motion, and to decrease the patient's level of pain. Unfortunately, motivating a patient to comply with a prescribed exercise regime can be difficult.

Lack of patient motivation to comply with prescribed exercises is a hindrance to any therapy regimen. Statistics have shown that a motivational program combined with the right exercise program can increase patient compliance by as much as 30%. It is desirable, therefore, to provide a device or system that motivates a patient to perform his or her prescribed exercises.

In addition to lack of motivation, another problem that arises relates to a patient's actual performance of the exercises. If a patient performs the prescribed exercises incorrectly, little or no benefit will be gained from exercising and the full benefits of the therapy regime will not be realized. In addition, improperly performed exercises can, in some cases, do more harm than good. It is desirable, therefore, to have a device or system that can provide feedback to the patient regarding the manner in which they are performing their exercises. Preferably, the feedback will be provided to the patient in real-time during the exercise workout to allow the patient to correct and adjust how they are doing the exercises so that the prescribed exercises are properly performed.

In general, self reported information concerning a patient's compliance with a prescribed exercise regime has limited value. If objective information were made readily available to the prescribing physician or physical therapist, a patient's therapy could be monitored and modified with much more certainty, and the effectiveness of each exercise could be quantitatively analyzed. Patient distance from their clinic would also become less relevant, since frequent visits to the clinic would become less necessary. A device and/or system of this type would be of great value to doctors and physical therapists.

Unfortunately, there is often no way for a physician or physical therapist to know if a patient is complying with the prescribed exercise regime or if the patient is performing their exercises correctly. It is desirable, therefore, to have an apparatus or system that provides information to physicians and physical therapists regarding a patient's compliance with a prescribed exercise program. It is also desirable to have a device or system that can provide information regarding how well the patient is performing the prescribed exercises. Preferably, the apparatus or system will allow for real-time monitoring of the patient during exercising and will also record the desired information and make it available for later use and analysis by the physician or physical therapist.

Another problem with providing a device that can be used during exercise relates to the very nature of the exercises themselves. Exercises prescribed for patients suffering from low back pain can generally be broken down into two categories, namely strengthening exercises and stretching exercises. Strengthening exercises serve to increase muscle strength while stretching exercises serve to increase range of motion.

Examples of strengthening exercises that are typically prescribed for patients suffering from low back pain include four point extension exercises, side exercises, general upright exercises, prone exercises, and bridging exercises. For many of the strengthening exercises, it is desirable for the patient to maintain his or her lumbar spine in a stable and static position. Thus, for these types of exercises, it is generally desirable to have a device or system that can detect small movements in a patient's spine.

Examples of stretching exercises that are typically prescribed for low back pain patients include back bending, the cat stretch, and the hip extension. For these types of exercises, it is desirable for the patient to increase their range of motion and therefore these types of exercises do not usually involve a static and stable spine. To the contrary, it is desirable for the patient to have a relatively large range of both flexion/extension motion and lateral motion while performing the stretching exercises.

It is desirable, therefore, to have a device that can accurately measure both small incremental movements of a patient's spine as well as spine position over a relatively large range of motion. Preferably, the device can accurately measure the degree of patient bending in both the midsagittal (median) and coronal (frontal) planes between the sacrum and the thoracic region of the spine. In other words, it is desirable to have a device that can detect, monitor and measure flexion/extension and lateral movements of a patient's spine.

It is desirable to have a device or system that can also be used in other areas where detecting, monitoring, measuring and recording an individual's movement or range of motion is important, including recreational sports, such as golf, and industrial activities involving repetitive spinal motion.

Although many prior art devices have been developed for detecting and monitoring a patient's spine movement, they all suffer from one or more problems or deficiencies that have kept them from being commercialized for wide spread home usage by patients. Generally, the known prior art devices are either too complicated for home use by patients or they are too expensive to be generally provided to patients for home use. It is also desirable therefore to have a device or system that is simple in both construction and use. The device will desirably be simple enough to allow for operation by a patient in a non-clinical setting (i.e., without a therapist's supervision) such as at the patient's home. Preferably, the cost of the device or system will also be such that the device or system can be provided for wide scale distribution to patients for use both in a clinical setting and at home.

SUMMARY OF THE PRESENT INVENTION

According to a first aspect of the invention, an apparatus for monitoring the movement of a patient's spine includes a vertical member, a first sensor and a second sensor. The first sensor is mounted to the vertical member and is disposed to monitor flexion and extension motion of the patient's spine in the midsagittal plane. The second sensor is mounted to the vertical member and is disposed to monitor lateral motion of the patient's spine in the frontal plane.

Other principal features and advantages of the invention will become apparent to those skilled in the art upon review of the following drawings, the detailed description and the appended claims.

BRIEF DESCRIPTION OF THE DRAWINGS

The drawings, which constitute a part of the specification, are as follows.

Figure 1:
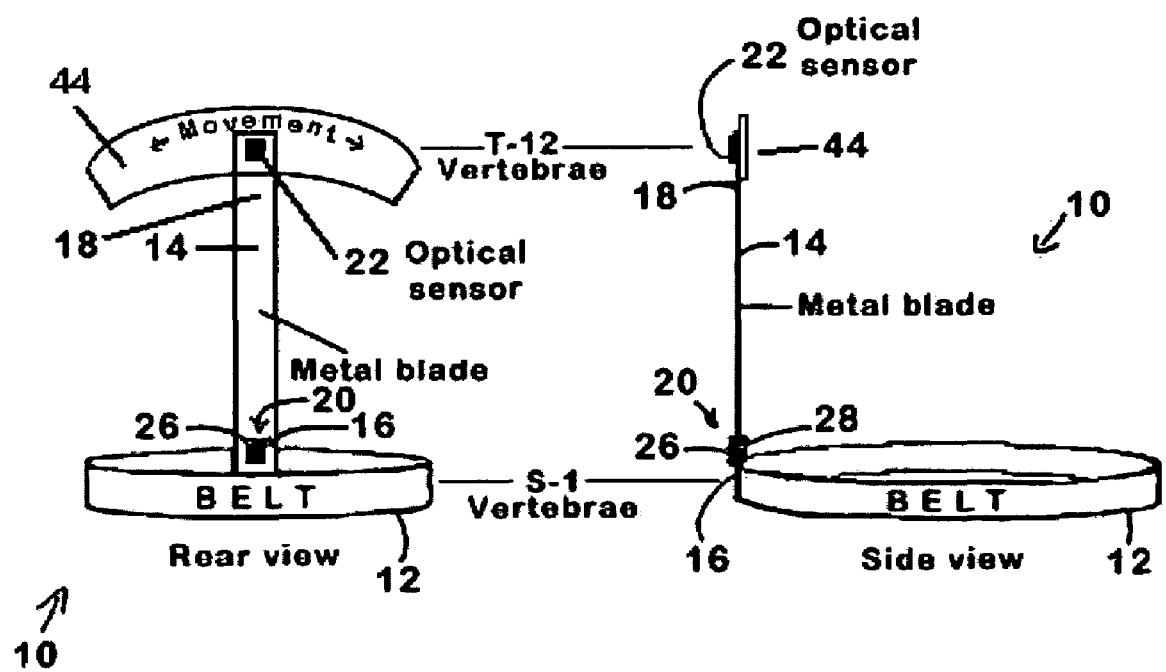
FIG. 1(a) is a rear view of a wearable spine monitoring device according to one embodiment of the present invention.
FIG. 1(b) is a side view of the wearable spine monitoring device shown in FIG. 1(a)

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. Like reference numerals are used to indicate like components.

DETAILED DESCRIPTION OF THE PREFERRED EMBODIMENTS

While the present invention will be illustrated with reference to a particular apparatus and system for monitoring a patient's range of motion having a particular configuration and particular features, the present invention is not limited to this configuration or to these features and other configurations and other features can be used. Also, although the present invention will be illustrated with reference to monitoring and detecting motion of the lumbar spine region, the present invention is not limited to only that region of the body and may have application to other regions of the body, including other regions of the spine.

The present invention is also not limited to use by patients with lower back pain or by patients involved in a therapeutic exercise program. To the contrary, the present invention can also be used in other applications and in other areas where it is desirable to detect, monitor, measure and/or record an individuals movement or range of motion. For example, the present invention could be used in the sport of golf to help individuals improve their golf swing. The present invention could also be used to monitor the movement and range of motions undertaken by employees working in various factory jobs. The information obtained could be used, for example, to identify extreme or repetitive motions that could be potentially damaging to a person's spine.

Generally, the present invention involves an apparatus and method for detecting, monitoring, measuring and/or recording information regarding the movement and range of motion of a patient's spine. In one embodiment of the present invention, movement and range of motion is monitored in both the midsagittal plane (known as flexion and extension) and in the frontal or coronal plane (known as lateral movement). In other embodiments, however, the invention only measures movement and range of motion in one of these planes.

The invention includes a wearable device having a vertical member in the form of a thin metal strip or blade. The lower end of the thin vertical member is attached to a belt or strap that fits snugly around the patient's waist (at approximately the height of the 1st sacral vertebrae). The thin vertical member extends upward in this embodiment from the sacrum to the thoracic region of the spine.

Mounted at or near the lower end of the vertical member is a first sensor (comprised of a plurality of strain gages in one embodiment). This sensor detects and monitors movement and motion in the midsagittal plane (e.g., flexion and extension motion). A second sensor is mounted at or near the top of the vertical member in this embodiment. This sensor detects and monitors lateral movement and motion in the frontal plane (also referred to as the coronal plane). The sensor mounted near the top of the vertical member in this embodiment is an optical mouse type sensor.

It should be noted that the present invention is not limited to the specific types of sensors described herein. Other embodiments of the present invention may use other types of sensors. For example, in an alternative embodiment of the present invention, the optical mouse type sensor is replaced by an inclinometer or a potentiometer.

The sensors and vertical member are disposed inside of the pocket of a corset or girdle in one embodiment. The corset is designed to fit snugly around the patient's torso between the patient's sacrum and thoracic region thereby helping to keep the vertical member in the proper position relative to the patient's spine during exercise. The pocket is lined with a low friction coating of some sort, such as Teflon, to help prevent the vertical member and the sensors from getting caught inside of the pocket during the performance of exercises by the patient.

The various sensors used in this embodiment are in electrical communication with a computer. The computer is used to record the patient's vertebral movements. The computer can also provide motivational feedback to the patient in real-time, such as in the form of a game, thus making the exercises more enjoyable for the patient.

A wearable spine monitoring device 10 according to one embodiment of the present invention is shown in FIG. 1. Wearable monitoring device 10 includes a nylon woven belt or strap 12 (although other types of belts or straps could be used) and a vertical member 14 attached at its lower end 16 to belt 12. Vertical member 14 in this embodiment is a thin stainless steel blade which is approximately 12.5 millimeters wide, 206 millimeters long, and 0.4572 millimeters thick.

Near the lower end 16 of vertical member 14 is mounted a first sensor 20 (actually a plurality of sensors in this embodiment) for measuring flexion and extension of the patient's lumbar spine in the midsagittal plane. A second sensor 22 is mounted at or near the opposite end 18 (the upper or top end) of vertical member 14 and provides for measurement of lateral movement (or motion) in the frontal (or coronal) plane. The total length of vertical member 14, including lateral motion sensor 22, extending above belt 12, is approximately 190.5 millimeters.

It should be noted that the dimensions of vertical member 14 make it susceptible to bending in the midsagittal plane with the patient during flexion and extension of the patient's lumbar spine. On the other hand, the same dimensions of vertical member 14 essentially prevent it from flexing or bending in the frontal plane during lateral bending by the patient. As a result, second sensor 22 mounted at or near the top of vertical member 14 remains relatively stationary in the frontal plane during lateral bending by the patient.

The base or lower end 16 of vertical member 14 in this embodiment is sandwiched between two thin pieces or plates of stainless steel (not shown), each about 0.50 millimeters thick. In this embodiment, the two stainless steel plates enclose the lower 40 millimeters of vertical member 14 and help to create a stable base approximately 7 millimeters away from flexion/extension sensor 20. The stable base provided by the plates helps to provide proper measurement of spine movement. This is because the stainless steel plates help eliminate stress concentrations that would be created if stainless steel blade 14 were punctured in this embodiment. Such stress concentrations could lead to a failure of vertical member 14, including loss of spring characteristics, which in turn could lead to decreased output from flexion/extension motion sensor 20.

The "blade sandwich" is attached to belt 12 in this embodiment so that vertical member 14 generally stays perpendicular to belt 12 in the frontal (coronal) plane during exercise. Belt 12 is worn around the waist (approximately at the height of the 1st sacral vertebrae), with base 16 of vertical member 14 centered in the middle of the patient's back (approximately at the height of the 12th thoracic vertebrae). Belt 12 has a buckle or clasp (not shown) in the front that allows adjustment on both ends of the belt in one embodiment of the present invention.

It should be noted that the present invention is not limited to the particular dimensions discussed herein and those dimensions are provided for illustrative purposes only. Other embodiments of the present invention would have other dimensions, one or more of which might be greater than or less than the dimension described herein. To some extent, the dimensions are dependent on the size and shape of the particular patient who will be using a device in accordance with the invention.

It should also be understood that the present invention is not limited to the use of a thin stainless steel member to support the sensors. The present invention is also not limited to the use of a vertical member. In other embodiments, members having other sizes, shapes and/or other orientations are used to support the various sensors that are used to detect and monitor patient motion and movement in the various planes.

Figure 2:
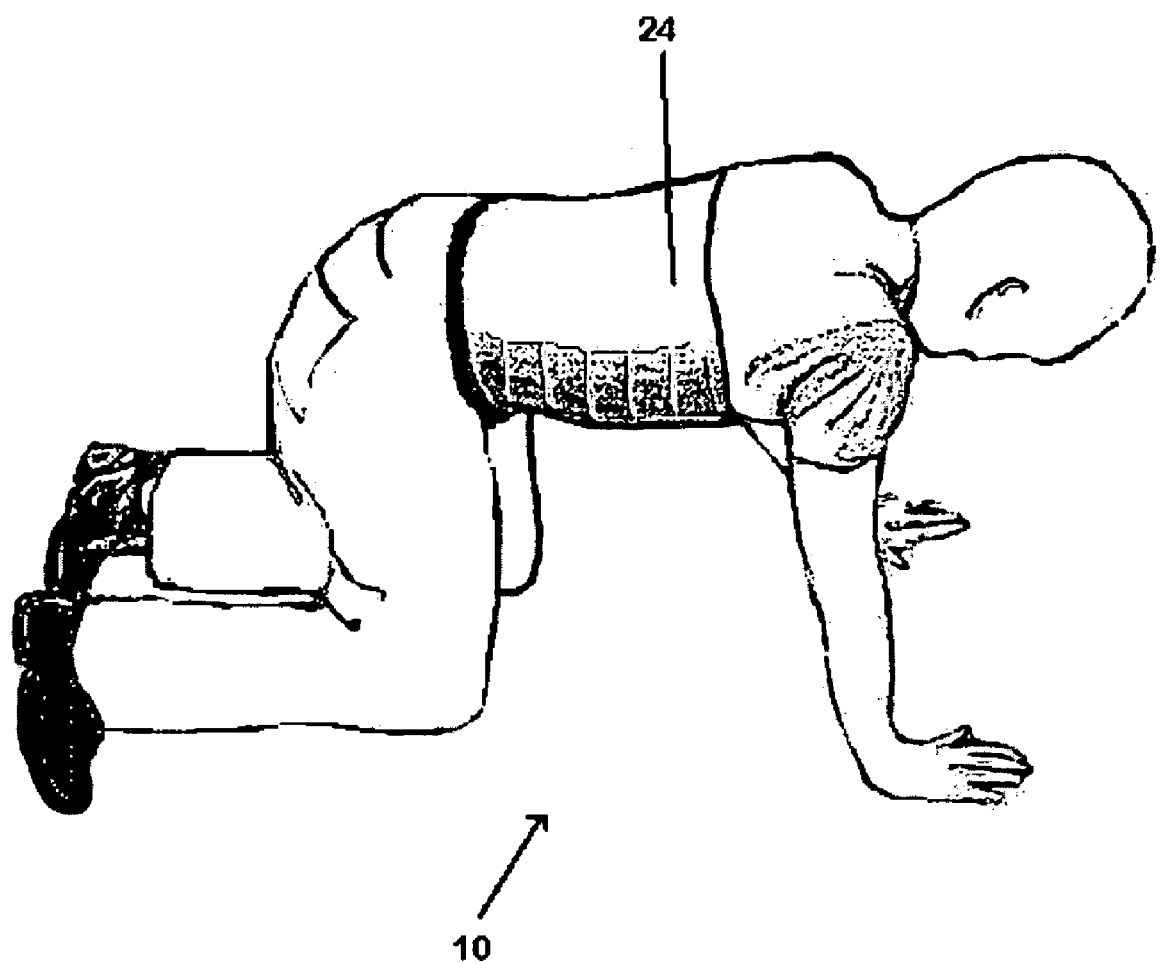
FIG. 2 is a side view of a spine monitoring device worn by a patient according to a second embodiment of the present invention.

The entire monitoring device 10 is contained inside of a girdle or corset 24 (see FIG. 2). Girdle 24 holds vertical member 14 against the body of the patient in a manner that allows girdle 24 to move independent of belt 12 and vertical member 14 while still enclosing vertical member 14. Girdle 24 generally covers the thoraco-lumbar region of the patient's back.

Vertical member 14 and lateral motion sensor 22 are enclosed in a pocket (not shown) in girdle 24 in this embodiment. The pocket is lined with a low friction coating (such as Teflon) to allow vertical member 14 and sensor 22 to move freely. In general, this pocket would be shaped so as to not impede vertical member 14 in any way. Thus, the pocket would generally accommodate the normal movement and bending of vertical member 14 along the patient's back during flexion or extension in the midsagittal plane and would not place any lateral forces on vertical member 14 during lateral movement of the patient's spine in the frontal plane.

In the embodiment shown in FIG. 1, flexion/extension sensor 20 is comprised of two dual strain gages 26, 28 (e,.g., each includes a pair of strain gages) which are mounted approximately 45 millimeters from the lower end 16 of vertical member 14 in this embodiment. Dual strain gage 26 is mounted on one side (the front side) of vertical member 14 while the other dual strain gage 28 is mounted on the other side (the back side) of vertical member 14 directly opposite first dual strain gage 26.

The four strain gages affixed to vertical member 14 in this embodiment are electrically connected in a full Wheatstone bridge configuration to detect flexion and extension movement of the spine. The operation of strain gages and strain gages configured in a full Wheatstone bridge configuration are well understood and their operation will only be described briefly herein.

In general, a strain gage is an electrical sensor whose resistance changes in proportion to a change in the length (and therefore strain) of the conductors located inside of the strain gage. The resistance R of a strain gage's conductor is:

$$R = \rho l/A$$

where R=resistance of the strain gage conductor in ohms, $\rho$=resistivity of the strain gage conductor in ohms/meter, l=length of the strain gage conductor in meters, and A=cross-sectional area of the strain gage conductor in meters$^2$. Thus, an increase in the length l of the strain gage conductor causes an increase in the overall resistance of the strain gage. As long as the strain gage conductors remain well below their elastic limit during the application of strain, there is a wide range within which the increase in resistance is linearly proportional to the increase in length and correspondingly linearly proportional to the strain applied.

Though there are several types of strain gages that are commercially available, the embodiment shown in FIG. 1 uses bonded strain gages. Bonded strain gages are made from wires or foil with a plastic backing. In other words, the strain gage is fixed to the structural element, in this case vertical member 14, on which strain measurement is needed. One such dual strain gage that has been shown to work is identified as standard part no. EA-O6-125PC-350 but other strain gages can also be used.

Figure 3:
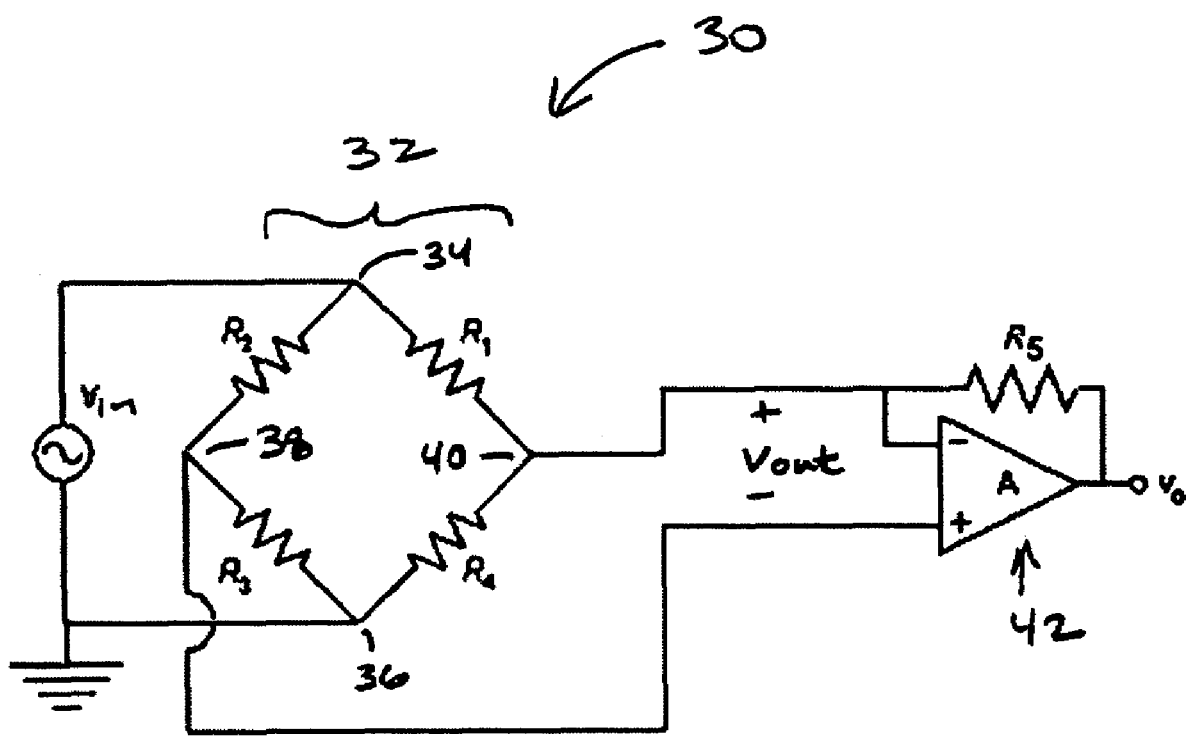
FIG. 3 is an electrical schematic view of a Wheatstone bridge circuit for use with the wearable spine monitoring device shown in FIG. 1(a).

As previously mentioned, each of the four strain gages is connected into a full Wheatstone bridge circuit 30 as illustrated in FIG. 3. Resistors R1, R2, R3 and R4 represent the variable resistances of each of the four strain gages. The excitation signal Vin to the bridge circuit 30 is provided between nodes 34 and 36 of bridge 32. In this case the input signal is a voltage Vin applied between node 34 and ground (e.g., node 36 in this embodiment is grounded).

The output signal Vout of bridge 32, again in this case a voltage, is obtained across nodes 38 and 40 of bridge 32. The output voltage Vout is fed into an differential operational amplifier 42. A 150 k-ohm resistor R5 is connected across the input and output of the amplifier to account for DC offset. The purpose of this resistor is to ensure that the neutral position of vertical member 14 corresponds to a zero voltage output of bridge circuit 30.

The voltage input source Vin for circuit 30 and for the "offset" resistor in this embodiment is 5 volts dc. Circuit 30 also has 15 volts powering differential op amp 42. These voltages can be provided by a power supply attached to the circuit, by batteries, or by any other suitable source of power.

The output from amplifier 42 is generally connected to a computer through an analog-to-digital (ADC) converter (not shown). One such ADC is the DI 194RS Starter Kit supplied by Dataq Instruments of Akron, Ohio. The DI 194RS is a 4 channel, ±10 Volt, 10 bit serial port data acquisition instrument that includes waveform recording, playback, and analysis software. The output of the ADC is compatible with several computer programming languages including LabVIEW which is used in one embodiment of the present invention and which is described more fully below.

The lateral motion sensor 22 for measuring lateral movement (or motion) in the frontal (or coronal) plane is mounted on vertical member 14 near the upper end 18 of vertical member 14 in the embodiment shown in FIG. 1. Sensor 22 is an optical mouse type sensor (e.g, components from an optical mouse can be used) such as is incorporated into the Atek Super Mini Optical Mouse supplied by Atek, Inc. of Santa Ana, Calif. Optical mouse type sensor 22 is disposed on vertical member 14 such that it is located at approximately the 12th thoracic vertebrae when monitoring device 10 is worn by a patient. Optical sensor 22 in this embodiment is 19 millimeters wide, 60 millimeters long and 9.5 millimeters thick.

The operation of optical mice, like the operation of strain gages, is well understood and thus their operation will only be described briefly herein. In general, an optical mouse uses a tiny camera to take a large number of pictures every second. Most optical mice utilize a small, red light-emitting diode (LED) that bounces light off a surface onto a complimentary metal-oxide semiconductor (CMOS) sensor. The CMOS sensor sends each image to a digital signal processor (DSP) for analysis. The DSP, operating at speeds as high as 18 MIPS (million instructions per second), is able to detect patterns in the images and can see how those patterns have moved since the previous image was taken. Based on the change in patterns over a sequence of images, the DSP determines how far and in what direction the mouse has moved and sends the corresponding coordinates to a computer. The computer moves the cursor on the screen based on the coordinates received from the mouse. This happens hundreds of times each second, making the cursor appear to move very smoothly.

The patient monitoring device shown in FIG. 1 includes a track 44 which is either mounted directly on the patient's back beneath optical mouse sensor 22 or, if optical mouse sensor 22 is contained inside of a corset pocket, is mounted inside of the corset pocket beneath optical sensor 22. Thus, in this embodiment, it is movement of track 44 beneath fixed optical mouse sensor 22 that is detected by the optical sensor.

One benefit to using an optical mouse as a lateral movement sensor is that optical mice have the capability to work on almost any type of surface. Thus, in other embodiments of the present invention, no track is provided beneath the optical mouse sensor. In these embodiments, the optical mouse simply senses movement of the surface of the patient's back or, if contained in a corset pocket, movement of the inside surface of the pocket of the corset.

Another advantage to using an optical mouse is that it can electronically communicate with a personal computer in an easy and simple manner.

LabVIEW is a computer program language that is used in one embodiment of the present invention to acquire data from flexion/extension sensor 20 and from lateral motion sensor 22. The data, once acquired from the various sensors, is displayed on a computer as a waveform graph or in some other form usable by a patient or a physician.

To acquire data from the strain gages as previously described herein, an active X LabVIEW option using Ultima Serial is used. It is a sub visual instruments (VI) program that detects signals from the ADC and puts them in a format compatible with LabVIEW. From these signals, a graph can be generated that shows in various forms the position of the patient's spine during exercise.

The signal from the optical mouse described above can also be interpreted by the LabVIEW program which actually detects the position of the cursor on the screen by pixels. The xy pixel coordinates can be used to show lateral movements of the patient.

Operation of monitoring device 10 to detect and monitor lumbar spine movement or motion will now be described. Flexion and extension of the lumbar spine in the midsagittal plain causes vertical member 14 to flex or bend in the midsagittal plane. The strain gage sensors 26, 28 in turn detect the strain placed on vertical member 14 as it flexes forward and backwards with the patient.

The strain placed on strain gages 26 and 28 causes those devices to change their electrical resistance as described above. In other words, the electrical resistance of each strain gage changes as the patient moves and bends in the midsagittal plane. The change in resistance of each strain gage unbalances Wheatstone bridge 32 of circuit 30. As a result, an output voltage is provided at the output of circuit 30. The output voltage is provided to a computer where it is used to display the position and movement of the patient's spine.

Lateral movement (in the frontal plane) is quantified using optical mouse sensor 22. As a patient bends sideways towards the right or left (again in the frontal plane), vertical member 14 remains substantially vertical and stationary in the frontal plane. This is because thin vertical member 14 does not flex in the lateral direction. The horizontal distance the patient's spine moves, with respect to lateral motion sensor 22, determines the angle that the lumber spine is bent in the frontal plane.

Wearable monitoring device 10 shown in FIG. 1 according includes several features that make it well adapted for use in monitoring and measuring lumbar spine movement and range of motion. First, the strain gages mounted on the bendable metal surface of vertical member 14 are extremely small, lightweight, inexpensive, and accurate. Second, optical mouse sensor 22 mounted at the top end 18 of vertical member 14 is also inexpensive, relatively small, and has an output ready for use by a personal computer. Third, the metal stainless steel blade that comprises vertical member 14 is easily bendable in the midsagittal plane; however, vertical member 14 does not flex or bend laterally in the frontal plane.

Numerous modifications may be made to the present invention which still fall within the intended scope hereof. Thus, it should be apparent that there has been provided in accordance with the present invention an apparatus and method of for detecting, monitoring, measuring, and recording the movement and range of motion of a patient's spine that fully satisfies the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The embodiments of the invention in which an exclusive property or privilege is claimed are defined as follows:

1. An apparatus for monitoring the movement of a patient's spine comprising:
   an elongated member adapted to be disposed longitudinally adjacent to the patient's spine and further adapted to be flexible in the midsagittal plane and substantially inflexible in the frontal plane;
   a first sensor mounted to the elongated member and disposed to monitor flexion and extension motion of the patient's spine in the midsagittal plane, wherein the first sensor includes at least one strain gage; and a second sensor mounted to the elongated member and disposed to monitor lateral motion of the patient's spine in the frontal plane, wherein the second sensor is an optical sensor.

2. An apparatus for monitoring the movement of a patient's spine comprising:
an elongated member adapted to be disposed longitudinally adjacent to the patient's spine and further adapted to be flexible in the midsagittal plane and substantially inflexible in the frontal plane;
a first sensor mounted to the elongated member and disposed to monitor flexion and extension motion of the patient's some in the midsagittal plane; and
a second sensor mounted to the elongated member and disposed to monitor lateral motion of the patient's some in the frontal plane, wherein the second sensor is an optical sensor, and further wherein the second sensor is an optical mouse sensor.

3. An apparatus for monitoring the movement of patient's spine comprising:
an elongated member adapted to be disposed longitudinally adjacent to the patient's spine and further adapted to be flexible in the midsagittal plane and substantially inflexible in the frontal plane, wherein the elongated member has a first end and a second end opposite the first end;
a first sensor mounted to the elongated member and disposed to monitor flexion and extension motion of the patient's spine in the midsagittal plane, wherein the first sensor is mounted to the elongated member near the first end; and
a second sensor mounted to the elongated member and disposed to monitor lateral motion of the patient's spine in the frontal plane, wherein the second sensor is mounted to the elongated member near the second end.

4. An apparatus for monitoring the movement of a patient's spine comprising:
an elongated member adapted to be disposed longitudinally adjacent to the patient's spine and further adapted to be flexible in the midsagittal plane and substantially inflexible in the frontal plane;
a first sensor mounted to the elongated member and disposed to monitor flexion and extension motion of the patient's spine in the midsagittal plane, wherein the first sensor is adapted to be disposed along the patient's spine at approximately the location of the 1st sacral vertebrae; and
a second sensor mounted to the elongated member and disposed to monitor lateral motion of the patient's spine in the frontal plane, wherein the second sensor is adapted to be disposed along the patient's spine at approximately the location of the 12th thoracic vertebrae.

5. An apparatus for monitoring the movement of a patient's spine comprising:
an elongated member adapted to be disposed longitudinally adjacent to the patient's spine and further adapted to he flexible in the midsagittal plane and substantially inflexible in the frontal plane;
a first sensor mounted to the elongated member and disposed to monitor flexion and extension motion of the patient's spine in the midsagittal plane;
a second sensor mounted to the elongated member and disposed to monitor lateral motion of the patient's spine in the frontal plane; and
a corset wearable by the patient and having a pocket, wherein the elongated member is substantially disposed inside of the pocket.

6. The apparatus of claim 5 wherein the second sensor is disposed inside of the pocket.

7. The apparatus of claim 6 wherein the corset includes a track disposed inside of the pocket, and further wherein the second sensor is an optical sensor disposed to detect movement of the track as the patient's spine moves laterally in the frontal plane.

8. An apparatus for monitoring the movement of a patient's spine comprising:
an elongated member adapted to be disposed longitudinally along the patient's spine, wherein the elongated member has a first end and a second end opposite the first end;
a first sensor mounted to the elongated member and disposed to monitor flexion and extension motion of the patient's lumbar spine in the midsagittal plane, wherein the first sensor is mounted to the elongated member near the first end; and
a second sensor mounted to the elongated member and disposed to monitor lateral motion of the patient's lumbar spine in the frontal plane, wherein the second sensor is an optical sensor, and further wherein the second sensor is mounted to the elongated member near the second end.

9. The apparatus of claim 8 wherein the second sensor is an optical mouse sensor.

10. The apparatus of claim 8 further comprising a computer in electrical communication with the second sensor, wherein the computer includes a display having a cursor, wherein the second sensor controls movement of the cursor, and further wherein the computer interprets the position of the cursor to graphically show lateral movement of the patient's spine on the display.

11. The apparatus of claim 8 further comprising a corset wearable by the patient, wherein the corset includes a pocket and a track disposed inside of the pocket, and further wherein the second sensor is disposed inside of the pocket to detect movement of the track as the patient's spine moves laterally in the frontal plane.

* * * * *